US009970833B2

(12) United States Patent
Georgeson et al.

(10) Patent No.: US 9,970,833 B2
(45) Date of Patent: May 15, 2018

(54) WITNESS MATERIAL AND METHOD FOR MONITORING THE ENVIRONMENTAL HISTORY OF AN OBJECT

(71) Applicant: The Boeing Company, Chicago, IL (US)

(72) Inventors: Gary E. Georgeson, Tacoma, WA (US); Morteza Safai, New Castle, WA (US)

(73) Assignee: The Boeing Company, Chicago, IL (US)

(*) Notice: Subject to any disclaimer, the term of this patent is extended or adjusted under 35 U.S.C. 154(b) by 212 days.

(21) Appl. No.: 14/259,519

(22) Filed: Apr. 23, 2014

(65) Prior Publication Data
US 2015/0308907 A1    Oct. 29, 2015

(51) Int. Cl.
*G01L 1/24* (2006.01)
*G01K 11/12* (2006.01)
*G01N 21/64* (2006.01)

(52) U.S. Cl.
CPC ........... *G01L 1/24* (2013.01); *G01K 11/12* (2013.01); *G01N 21/64* (2013.01); *G01N 2021/6497* (2013.01)

(58) Field of Classification Search
CPC ......... G01L 1/24; G01K 11/12; G01N 21/64; G01N 2021/6497
USPC ........... 116/200, 201, 203, 207, 216, 215; 250/461.1, 458.1, 208.1; 436/2; 374/162, 165
See application file for complete search history.

(56) References Cited

U.S. PATENT DOCUMENTS 2,249,867 A * 7/1941 Snelling ............... G01N 31/222
                                                                116/206
2,387,512 A * 10/1945 Hilberg .................... C09D 5/22
                                                                116/DIG. 14
2,417,384 A * 3/1947 Switzer .................... F21K 2/00
                                                                101/211
(Continued)

FOREIGN PATENT DOCUMENTS

EP          0538580      4/1993
GB          2194062      2/1988
(Continued)

OTHER PUBLICATIONS

Nevadunsky, J. J. et al.; "Early Fatigue Damage Detection in Composite Materials", Journal of Composite Materials, 1975, vol. 9, pp. 394-408.
(Continued)

*Primary Examiner* — R. A. Smith
*Assistant Examiner* — Tania Courson
(74) *Attorney, Agent, or Firm* — Thompson Hines LLP (57) ABSTRACT

A witness material for monitoring an environmental history of an object may include a material containing a dye of a type that fluoresces in response to actinic radiation in one or both of a shift in color and a change in intensity when subjected to a predetermined stress above a predetermined level; and the material forming a coating on one or more of an outer container for the object, an inner container for the object, a tape that is applied to an outer container for the object, a tape that is applied to an inner container for the object, a shrink wrap enclosing the object, an outer surface of the object, and an inner surface of the object.

21 Claims, 3 Drawing Sheets

(56) References Cited

U.S. PATENT DOCUMENTS

| | | | | |
|---|---|---|---|---|
| 2,674,221 A * | 4/1954 | Tinsley | | G01C 9/10 |
| | | | | 116/215 |
| 2,712,507 A * | 7/1955 | Green | | B41M 5/165 |
| | | | | 101/DIG. 29 |
| 2,889,799 A * | 6/1959 | Korpman | | A61B 19/02 |
| | | | | 116/207 |
| 3,078,182 A * | 2/1963 | Crone, Jr. | | A61L 2/28 |
| | | | | 116/207 |
| 3,239,366 A * | 3/1966 | Miller | | B41M 5/38235 |
| | | | | 101/470 |
| 3,243,303 A * | 3/1966 | Johnson | | G01K 3/04 |
| | | | | 116/207 |
| 3,311,084 A * | 3/1967 | Edenbaum | | A61L 2/28 |
| | | | | 116/207 |
| 3,667,916 A * | 6/1972 | Sliva et al. | | G01K 11/12 |
| | | | | 101/35 |
| 3,744,295 A | 7/1973 | Allinikov | | |
| 4,003,245 A * | 1/1977 | Ogata | | G01L 1/247 |
| | | | | 116/201 |
| 4,105,583 A | 8/1978 | Glover et al. | | |
| 4,188,437 A * | 2/1980 | Rohowetz | | A61L 2/28 |
| | | | | 116/207 |
| 4,212,153 A * | 7/1980 | Kydonieus | | G04F 1/00 |
| | | | | 116/207 |
| 4,273,674 A | 6/1981 | Ligon et al. | | |
| 4,292,916 A * | 10/1981 | Bradley | | G01K 3/04 |
| | | | | 116/205 |
| 4,344,909 A | 8/1982 | De Blauwe | | |
| 4,470,122 A | 9/1984 | Sarr | | |
| 4,516,679 A * | 5/1985 | Simpson | | B65D 75/52 |
| | | | | 206/459.1 |
| 4,661,305 A | 4/1987 | Carlomagno | | |
| 4,675,161 A * | 6/1987 | Hashimoto | | C12Q 1/22 |
| | | | | 116/207 |
| 4,677,473 A | 6/1987 | Okamoto et al. | | |
| 4,717,674 A | 1/1988 | Sung | | |
| 4,834,909 A | 5/1989 | Nagel | | |
| 4,958,853 A * | 9/1990 | Doty | | B60R 22/16 |
| | | | | 116/203 |
| 4,963,415 A | 10/1990 | Carlson et al. | | |
| 5,100,802 A | 3/1992 | Mickols | | |
| 5,110,655 A * | 5/1992 | Engler | | A42B 3/061 |
| | | | | 2/5 |
| 5,234,732 A * | 8/1993 | Versic | | B32B 27/08 |
| | | | | 206/459.1 |
| 5,282,017 A | 1/1994 | Kasindorf et al. | | |
| 5,308,887 A * | 5/1994 | Ko | | C09J 4/00 |
| | | | | 428/446 |
| 5,323,652 A * | 6/1994 | Parker | | G01F 23/22 |
| | | | | 73/295 |
| 5,384,079 A | 1/1995 | Bur et al. | | |
| 5,424,841 A | 6/1995 | Van Gelder et al. | | |
| 5,425,824 A | 6/1995 | Marwick | | |
| 5,438,879 A * | 8/1995 | Reda | | G01B 11/162 |
| | | | | 73/800 |
| 5,472,092 A * | 12/1995 | Evert | | B65D 71/10 |
| | | | | 206/497 |
| 5,534,289 A * | 7/1996 | Bilder | | B05D 5/00 |
| | | | | 427/8 |
| 5,539,013 A | 7/1996 | Eckberg et al. | | |
| 5,756,356 A | 5/1998 | Yanagi et al. | | |
| 5,780,857 A | 7/1998 | Harju et al. | | |
| 5,790,718 A * | 8/1998 | Tenner | | B65B 61/26 |
| | | | | 206/459.5 |
| 5,817,945 A * | 10/1998 | Morris | | G01L 1/24 |
| | | | | 73/762 |
| 5,828,460 A | 10/1998 | Lucovsky et al. | | |
| 5,854,684 A | 12/1998 | Stabile et al. | | |
| 5,920,017 A * | 7/1999 | Pechersky | | G01B 11/162 |
| | | | | 73/762 |
| 6,029,421 A * | 2/2000 | Mellbin | | B65D 5/42 |
| | | | | 53/410 |
| H1843 H | 3/2000 | Bur et al. | | |
| 6,272,901 B1 * | 8/2001 | Takeuchi | | G01M 7/08 |
| | | | | 73/12.01 |
| 6,376,045 B1 * | 4/2002 | Wong | | C09J 7/0296 |
| | | | | 359/538 |
| 6,486,319 B1 | 11/2002 | Bohm et al. | | |
| 6,815,207 B2 * | 11/2004 | Yabuki | | G01N 31/222 |
| | | | | 116/311 |
| 6,848,389 B1 * | 2/2005 | Elsasser | | G01L 5/0052 |
| | | | | 116/203 |
| 6,941,818 B2 * | 9/2005 | Rakowski | | A63B 69/3661 |
| | | | | 473/278 |
| 7,050,535 B2 | 5/2006 | Georgeson et al. | | |
| 7,219,619 B2 * | 5/2007 | Fitzer | | G01P 15/036 |
| | | | | 116/203 |
| 7,219,799 B2 * | 5/2007 | Bonnette | | B65D 79/02 |
| | | | | 206/459.1 |
| 7,246,570 B2 | 7/2007 | Weng et al. | | |
| 7,351,467 B2 * | 4/2008 | Blonder | | A47G 19/2227 |
| | | | | 220/201 |
| 7,514,262 B2 * | 4/2009 | Ribi | | G01N 31/229 |
| | | | | 116/206 |
| 7,517,146 B2 * | 4/2009 | Smith | | G01K 3/04 |
| | | | | 116/207 |
| 7,647,809 B1 | 1/2010 | Cooney | | |
| 7,682,830 B2 * | 3/2010 | Prusik | | G01N 31/229 |
| | | | | 116/216 |
| 7,712,431 B2 | 5/2010 | Roche | | |
| 7,769,550 B2 * | 8/2010 | Hyodo | | G01L 1/24 |
| | | | | 702/42 |
| 7,913,640 B2 * | 3/2011 | MacDonald | | A61M 16/1045 |
| | | | | 116/200 |
| 7,963,694 B2 * | 6/2011 | Leute | | G01K 3/005 |
| | | | | 374/157 |
| 8,083,423 B2 * | 12/2011 | Roth | | B41J 2/32 |
| | | | | 400/120.01 |
| 8,432,537 B2 * | 4/2013 | Lam | | G01B 11/168 |
| | | | | 356/35 |
| 8,691,383 B2 | 4/2014 | Georgeson et al. | | |
| 8,711,002 B2 * | 4/2014 | Davis | | E21B 47/0001 |
| | | | | 116/227 |
| 8,720,278 B1 * | 5/2014 | Toivola | | G01B 11/16 |
| | | | | 73/762 |
| 9,085,052 B1 * | 7/2015 | Georgeson | | G01B 11/16 |
| 9,446,575 B1 * | 9/2016 | Georgeson | | G01B 11/16 |
| 9,518,879 B2 * | 12/2016 | Georgeson | | G01P 15/06 |
| 9,656,453 B2 * | 5/2017 | Georgeson | | B32B 41/00 |
| 2002/0000128 A1 * | 1/2002 | Williams | | G01N 21/91 |
| | | | | 73/762 |
| 2002/0154396 A1 | 10/2002 | Overbeck | | |
| 2003/0085151 A1 * | 5/2003 | Cleaver | | B65D 81/07 |
| | | | | 206/723 |
| 2004/0050740 A1 * | 3/2004 | Lewis | | G01N 21/78 |
| | | | | 206/459.1 |
| 2004/0121071 A1 | 6/2004 | Loyd et al. | | |
| 2004/0202812 A1 * | 10/2004 | Congard | | B42D 5/027 |
| | | | | 428/40.1 |
| 2005/0018898 A1 | 1/2005 | White et al. | | |
| 2005/0109984 A1 | 5/2005 | Potyrailo et al. | | |
| 2005/0158540 A1 * | 7/2005 | Sakai | | C09J 7/0207 |
| | | | | 428/349 |
| 2006/0056585 A1 | 3/2006 | Georgeson et al. | | |
| 2006/0116442 A1 | 6/2006 | Gallo et al. | | |
| 2006/0157195 A1 * | 7/2006 | Laurence | | B32B 27/36 |
| | | | | 156/307.1 |
| 2006/0286407 A1 * | 12/2006 | Amano | | B32B 27/08 |
| | | | | 428/690 |
| 2007/0197383 A1 * | 8/2007 | Koene | | B41M 5/124 |
| | | | | 503/201 |
| 2008/0209825 A1 | 9/2008 | Smith | | |
| 2008/0223152 A1 * | 9/2008 | Georgeson | | G01B 7/20 |
| | | | | 73/862.041 |
| 2009/0036304 A1 | 2/2009 | Misner et al. | | |
| 2009/0320742 A1 * | 12/2009 | Leute | | G01K 3/005 |
| | | | | 116/207 |
| 2010/0012018 A1 * | 1/2010 | Ribi | | C09B 57/10 |
| | | | | 116/207 |

(56) References Cited

U.S. PATENT DOCUMENTS

| | | | | |
|---|---|---|---|---|
| 2010/0192833 | A1* | 8/2010 | Yang | G01K 11/06 |
| | | | | 116/217 |
| 2010/0196637 | A1* | 8/2010 | Lippert | B29C 70/345 |
| | | | | 428/36.1 |
| 2011/0008587 | A1* | 1/2011 | Ruskin | B29C 66/474 |
| | | | | 428/192 |
| 2011/0123712 | A1 | 5/2011 | Becker | |
| 2011/0316712 | A1* | 12/2011 | McIver | G01M 5/0033 |
| | | | | 340/665 |
| 2012/0174853 | A1* | 7/2012 | Wilson | G01N 31/229 |
| | | | | 116/206 |
| 2012/0225294 | A1* | 9/2012 | Georgeson | B64D 45/00 |
| | | | | 428/402.2 |
| 2012/0275968 | A1 | 11/2012 | Puntambekar | |
| 2013/0061798 | A1* | 3/2013 | Ribi | A46B 15/0002 |
| | | | | 116/207 |
| 2013/0122594 | A1 | 5/2013 | Hughes et al. | |
| 2014/0273240 | A1* | 9/2014 | Georgeson | G01N 31/229 |
| | | | | 436/7 |
| 2015/0321496 | A1* | 11/2015 | Clayton | B41M 5/165 |
| | | | | 503/201 |
| 2015/0338296 | A1* | 11/2015 | Georgeson | G01B 11/16 |
| | | | | 116/212 |
| 2016/0076947 | A1* | 3/2016 | Ribi | C09B 57/10 |
| | | | | 250/474.1 |
| 2016/0146747 | A1* | 5/2016 | Degaetano | G01N 25/72 |
| | | | | 374/162 |
| 2016/0195437 | A1* | 7/2016 | Georgeson | G01K 11/12 |
| | | | | 374/162 |
| 2016/0279923 | A1* | 9/2016 | Georgeson | G01B 11/16 |
| 2016/0282198 | A1* | 9/2016 | Georgeson | G01N 21/64 |
| 2016/0282288 | A1* | 9/2016 | Degaetano | B29C 35/0288 |

FOREIGN PATENT DOCUMENTS

| | | |
|---|---|---|
| JP | 06-313738 | 11/1994 |
| WO | 0072055 | 11/2000 |

OTHER PUBLICATIONS

Richards, R. F. et al.; "Fire Detection, Location and Heat Release Rate Through Inverse Problem Solution. Part II: Experiment"; Fire Safety Journal, 1997, 28, pp. 351-378.

Stefani, F. D. et al.; "Thermochromic Fluorophores and Their NIR Laser Induced Transformation"; Chemistry of Materials, 2006, 18, pp. 6115-6120.

Lempereur, C. et al.; "Surface Temperature Measurement on Engine Components by Means of Irreversible Thermal Coatings"; Measurement Science and Technology, 2008, 19, 105501, 11 pages.

Khatibi, A. A. et al.; "On the Application of Liquid-Crystal Thermography for the Nondestructive Detection of Delamination in Composite Structures"; Polymer Composites, 2008, 29, pp. 798-803.

Feraboli, P. et al.; "Damage Resistance and Tolerance of Carbon/Epoxy Composite Coupons Subjected to Simulated Lightning Strike"; Composites: Part A, 2009, 40, pp. 954-967.

Extended European Search Report and Search Opinion, European Application No. 14158434.2 (dated Dec. 11, 2014).

Fisher, W. G. et al.; "Nondestructive Inspection of Graphite-Epoxy Composites for Heat Damage Using Laser-Induced Fluorescence", Applied Spectroscopy, vol. 49, No. 9, pp. 1225-1231 (Sep. 1995).

Seeboth, A. et al.; "Thermochromic Polymer Materials", Chinese Journal of Polymer Science, vol. 25, pp. 129-135.

Howie, T. et al., "Detection of Thermal Damage of CFRP Using Fluorescent Thermal Damage Probes", SAMPE Technical Conference, Charleston, SC (Oct. 23, 2012).

Air Force SBIR/STTR Innovation, SBIR Topic #AF04-133, RX2008-127.

International Searching Authority, "International Search Report and Written Opinion", International Application No. PCT/US2012/023127; dated May 18, 2012, (12 pages).

Soderquist, Arlen; Non-Final Office Action; U.S. Appl. No. 13/840,980 (dated Jan. 7, 2015).

Van Keuren, Edward et al., "Three-dimensional thermal imaging using two-photon microscopy"; Institute of Physics Publishing, 37 (2004) pp. 2938-2943.

Wu, Wen-Chung et al., "Enhancement of Aggregation-Induced Emission in Dye-Encapsulating Polymeric Micelles for Bioimaging", Advanced Functional Materials, 2010, 20, pp. 1413-1423.

Yang, Jun et al., "Excimer Formation in Uniaxially Stretched Polymer Films", Journal of AppliedPolymer Science, vol. 82, (2001), pp. 2347-2351.

Toivola, Ryan E. et al., "Stress Sensitive Fluorescent Dyes for Damage Detection in Aerospace Primers & Coatings", University of Washington Materials Science & Engineering, Seattle, WA 17 pages.

Georgeson, Gary Ernest et al., "Monitoring Composite Manufacturing and Repair Processes Using Chromatic Films", U.S. Appl. No. 13/791,207, filed Mar. 8, 2013.

U.S. Notice of Allowance, U.S. Appl. No. 13/840,980; (dated Mar. 15, 2016).

Edwards, G.R.; "Proceeding of the 2nd International Conference on Testing, Evaluation and Quality Control of Composites—TEQC 87"; pp. 3-10, Herriot, J., editor, Butterworths, London, England (1987).

Chen, Z. et al.; "Thermal Measurement Associated with Material Failure Using Thermochromic Coatings"; Experimental Techniques, 24. 3; ProQuest Central; pp. 29-32 (May-Jun. 2000).

Coleto, J. et al.; Phase Change Materials and Thermosensitive Painting: Application on Smart Thermal Protection Systems; IAC-06-C2[1].5.03; 12 pages (May 3, 2006).

Anonymous: "SAMPE Technical Papers Search Engine—SAMPE", Oct. 25, 2012, XP55390885, 2 pages; Retrieved from the Internet: URL:http://www.nasampe.org/page/searchengine#home/technicalpaperdetails/578ad888727949c01e519a24/ [retrieved on Jul. 14, 2017].

Howie et al: "Detection of Incipient Thermal Damage of CFRP Using Fluorescent Thermal Damage Probes", Oct. 23, 2012, XP55390878, Retrieved from the Internet: URL:https://depts.washington.edu/amtas/events/toray_13-03-29/howie.pdf [retrieved on Jul. 14, 2017].

EP, Office Action, European Patent Application No. 14158434.2; 5 pages (dated Jul. 21, 2017).

\* cited by examiner

WITNESS MATERIAL AND METHOD FOR MONITORING THE ENVIRONMENTAL HISTORY OF AN OBJECT

TECHNICAL FIELD

The present invention relates to non-destructive inspection techniques for detecting barely visible impact damage, and more particularly, to non-destructive inspection techniques that utilize a witness material that changes properties in response to an applied stress.

BACKGROUND

Objects that are shipped or stored in containers may be damaged by stress applied externally to the container. Such externally applied stress may take the form of one or more of rough handling, dropping, and bumping the container. Externally applied stress also may take the form of thermal cycles in which the container is subjected to extended periods of temperatures sufficiently high to damage the objects in the container or package. Damaging thermal cycles also may take the form of localized heating of less than the entire container to a temperature and for a time sufficient to damage the objects within.

Objects such as sensitive electronic instruments may be vulnerable to external stresses resulting from such rough handling, dropping and bumping, and also sensitive to exposure to high temperatures. Sensitive objects may include items such as chemicals, paints, biological substances, and live animals such as fish. These objects must be maintained within a relatively narrow temperature range when transported, and also may be susceptible to damage resulting from impacts to the containers in which they are shipped.

Such objects may arrive damaged to the recipient, but the exposure of the shipped or stored objects to damaging impacts, or to extended high temperatures during transportation or storage of the object, may not be readily apparent from an inspection of the object or the container. Consequently, it may difficult to prove that damage to the object within the container was sustained during the transportation of the object in the container, as opposed to the object being shipped in an original, damaged condition. It is therefore difficult in such circumstances to file a claim with a transporter of the object because there is no evidence that the damaging impact or damaging high temperature occurred during shipment.

Accordingly, there is a need for a non-destructive inspection technique that may readily and inexpensively indicate whether an object is subjected to stresses in the nature of impacts and/or damaging high temperatures during shipment.

SUMMARY

In an embodiment, a witness material for monitoring an environmental history of an object may include a material containing a dye of a type that fluoresces in response to actinic radiation in one or both of a shift in color and a change in intensity when subjected to a predetermined stress above a predetermined level; and the material forming a coating on one or more of an outer container for the object, an inner container for the object, a tape that is applied to an outer container for the object, a tape that is applied to an inner container for the object, a shrink wrap enclosing the object, an outer surface of the object, and an inner surface of the object.

In another embodiment, a system using witness material for monitoring an environmental history of an object may include a material containing a dye of a type that fluoresces in response to actinic radiation in or both of a shift in color and a change in intensity when subjected to a predetermined stress above a predetermined level; the material forming a coating on one or more of an outer container for the object, an inner container for the object, a tape that is applied to an outer container for the object, a tape that is applied to an inner container for the object, a shrink wrap enclosing the object, an outer surface of the object, and an inner surface of the object; and a source of the actinic radiation, the source configured to direct the actinic radiation on the coating after a predetermined event.

In yet another embodiment, a method for monitoring an environmental history of an object may include providing a material containing a dye of a type that fluoresces in response to actinic radiation in one or both of a shift in color and a change in intensity when subjected to a predetermined stress above a predetermined level; and forming a coating of the material on one or more of an outer container for the object, an inner container for the object, a tape that is applied to an outer container for the object, a tape that is applied to an inner container for the object, a shrink wrap enclosing the object, an outer surface of the object, and an inner surface of the object.

Other objects and advantages of the disclosed witness material and method for monitoring the environmental history of an object will be apparent from the following description, the accompanying drawings, and the appended claims.

DETAILED DESCRIPTION

Figure 1:
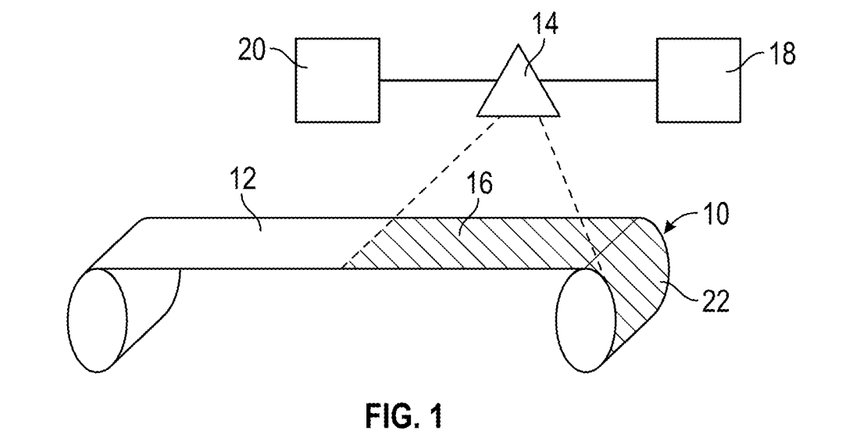
FIG. 1 is a schematic view of a witness material for monitoring an environmental history of an object, in which the witness material is in the form of a tape or shrink wrap sheet having a dye sprayed upon a surface of the tape or shrink wrap sheet.

As shown in FIG. 1, in one embodiment, the witness material for monitoring an environmental history of an object, generally designated 10, may be in the form of a tape 12 that is sprayed by a sprayer 14 to have a pattern or coating 16 of a material containing a dye or probe of a type that fluoresces in response to actinic radiation in one or both of a shift in color and a change in intensity when subjected to a predetermined stress above a predetermined level. In an embodiment, the coating 16 may include a mechanochromatic dye that is supplied to the sprayer from a source 18 of mechanochromatic dye. In an embodiment, the coating 16 may include a thermochromatic dye supplied to the sprayer 14 from a source 20 of thermochromatic dye. In other embodiments, the coating 16 may comprise a combination of a mechanochromatic dye and a thermochromatic dye.

In an embodiment, the source 18 may be a source of mechanochromatic dye obtainable under the brand AJNDE16, and the thermochromatic dye from source 20 may be obtained under the brand AJNDE17. Both AJNDE16 and AJNDE17 may be obtained from Soluxra, LLC located in Seattle, Wash. Other dyes or probes may be utilized, such as AJNDE30, AJNDE31, AJNDE32, AJNDE33 and AJNDE34, all available from the aforementioned Soluxra, LLC.

In an embodiment, the tape 12 may be an adhesive-backed tape. In another embodiment, the tape 12 may take the form of a sheet of shrink wrap material. As will be described, the tape 12 containing the coating 16, collectively referred to as a witness material or witness tape 22, may be applied to an object and/or a container for an object to be shipped or stored.

Figure 2:
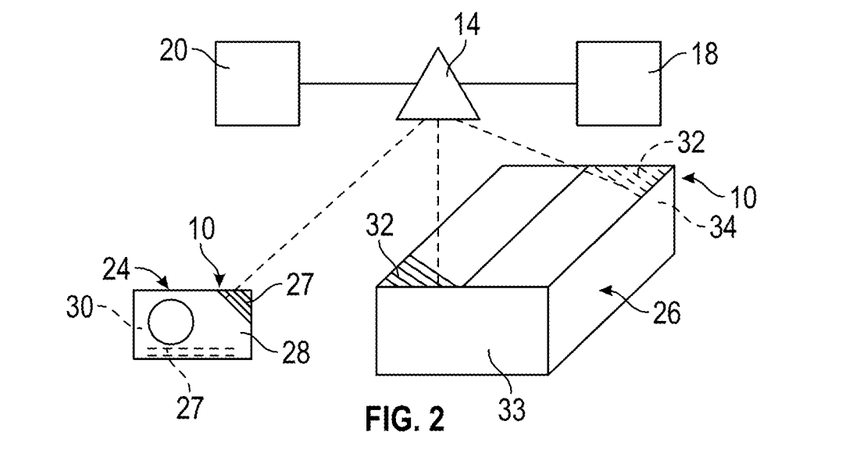
FIG. 2 is a schematic view of a witness material for monitoring an environmental history of an object in which the material containing a dye is applied to an object and a container for the object.

As shown in FIG. 2, in another embodiment the witness material 10 may be formed by spraying a coating 27 of witness material 10 in the form of mechanochromatic and/or thermochromatic dye from sources 18, 20, respectively, from the sprayer 14 on an object, generally designated 24, or a container, generally designated 26. The object 24 may be an object that is to be shipped and/or stored, and the container 26 may be a container for the object to be shipped and/or stored. Although container 26 is depicted as a box with flaps, the container may be any type of container, including a drum, an insulated foam chest, a cardboard box, a cardboard tube, a corrugated box, a plastic bag, and a bag or envelope made of Tyvek® (a trademark of E. I. du Pont de Nemours and Company). The coating 27 of witness material 10 may be applied to an external surface 28 of the object 24 to be shipped or stored, and/or to an internal surface 30 of the object. The coating 27 may be applied to the entire external and/or internal surfaces 28, 30 of the object 24, or to a selected portion or to selected portions of the external and/or internal surfaces. For example, the coating 27 may be applied to a selected external or internal corner or projection of the object 24, and/or to a selected external or internal edge of the object. The external or internal corner or edge of the object 24 may be selected as likely locations for sustaining a predetermined external stress, such as an impact or localized heating above a predetermined level.

Similarly, a coating 32 of witness material 10 may be applied to an external surface 33 of a container 26, or to an internal surface 34 of the container. The coating 32 may be applied to the entire external and/or internal surfaces 33, 34 of the container 26, or to a selected portion or portions of the external and/or internal surfaces, such as corners and/or edges of the container. Other locations on the object 24 and container 26 may be selected to receive coatings 27, 32 of witness material 10 and not depart from the scope of the disclosure. The external or internal corner or edge of the container 26 may be selected as likely locations for sustaining a predetermined external stress, such as an impact or localized heating above a predetermined level.

In an embodiment, the coatings 16, 27, and 32 of thermochromatic and/or mechanochromatic dye preferably are of a type that fluoresces in response to actinic radiation other than visible light. In a particular embodiment, the dyes AJNDE16 and AJNDE17 may be employed either separately, alternatively, in combination, or each in discrete areas on the object 28 or container 26. Such dyes may fluoresce in response to actinic radiation in the form of ultraviolet light. Also in an embodiment, the dye or dyes may be applied in the form of any one of the coatings 16, 27, and 32 embodied in a resin. In a particular embodiment, the resin may comprise di-glycidyl ether of bisphenol-A (DGEBA) with diethylenetriamine (DETA) as a curing agent. In an embodiment, the coatings 16, 27, 32 of witness material may contain a dye of a type that fluoresces in response to actinic radiation in one or both of a shift in color and a change in intensity when subjected to the predetermined stress, such as impact or heating, above a predetermined level for a predetermined time interval (in the case of a thermochromatic dye).

Figure 3:
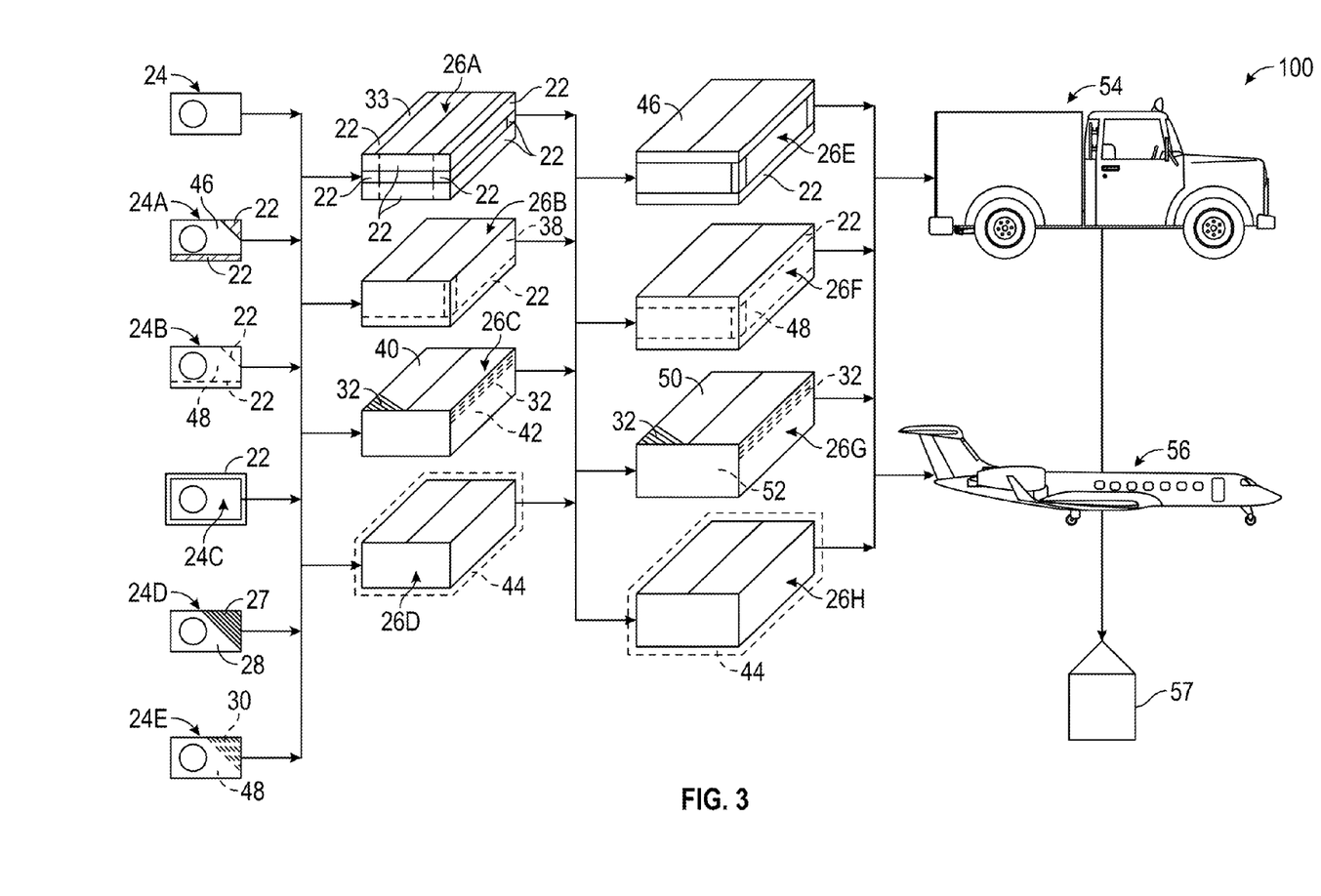
FIG. 3 is a schematic flow chart showing the process of transporting an object in which the object and/or a container for the object is coated with the disclosed witness material.

As shown in FIG. 3, the system, generally designated 100, for utilizing the witness material 10 may take many forms. In one form, the object 24 to be transported and/or stored does not receive a coating of witness material 10 and may be placed in a container 26A in which the outer surface 33 receives the tape 22 described with reference to FIG. 1. Application of the tape 22 may occur at the time the object 24 is packed within the container 26A, or the tape may be applied to the container 26A prior to packing. In one particular embodiment, an inventory of containers 26A may be maintained, each having tape 22, and used when needed. The tape 22 may be applied to selected areas of the container 26A, such as the corners and/or outer edges of the container 26A. In other embodiments, the tape 22 may be applied to flat surfaces of the outer surface 33 of the container 26A.

In another aspect of the system 100, a container 26B may be fitted with the witness tape 22 applied to an interior surface 38. The tape 22 may be applied to edges, corners, or flat surfaces of the interior surface 38. Witness tape 22 may be applied either at or prior to the time the object 24 is packed in container 26B. In another aspect of the system 100, a container 26C may receive a coating 32 of the witness material 10 sprayed on an exterior surface 40 thereof, and in addition, or alternatively, may receive a coating 32 on an interior surface 42. Coatings 32 may be applied at the time of packing the containers 26C, or prior to packing and the containers 26C and kept on hand. The coatings 32 may be applied by a spray device such as spray device 14 described with reference to FIG. 2, and may receive either thermochromatic dye, mechanochromatic dye, or a combination of both. In another aspect of the system 100, the container 26D may be wrapped in a shrink wrap 44 that has been sprayed with the witness material 16, as described with reference to FIG. 1.

In another aspect of the system 100, the object 24A itself may receive witness tape 22 at corners and projecting surfaces of the outer surface or surfaces 46 of the object. In another aspect of the system 100, the object 24B may receive witness tape 22 applied to an interior surface or surfaces 48. In yet another aspect of the system 100, the object 24C may be shrink wrapped with a sheet of shrink wrap 22 that has been coated with a coating 16 of witness material. The coating 22 may cover all of the sheet of shrink wrap 22, or only selected portions of the sheet.

In another aspect of the system 100, the object 24D may itself be spray coated with a coating 27 of witness material 16 on an external surface 28, or selected portions of the external surface. In still another aspect of the system 100, object 24E may have a coating 27 of witness material on an internal surface 30. The coatings 27, 30 on the external and/or internal surfaces 28, 30 may cover the entire surfaces, or selected portions of the surfaces. Objects 24A-24E may be treated with witness material 10 at the time of packing, or earlier, as at the time of assembly.

Each of the objects 24, 24A, 24B, 24C, 24D, and 24E may be placed within and packed in any one of the containers 26A, 26B, 26C, and 26D. Such packing may include adding packing material around the object 24, 24A-24E, then sealing the container 26, 26A-26D. Because the objects 24A-24E themselves may contain witness material 10 in the form of tapes 22 or in coatings 27, 30, it may not be necessary to treat the container 26 with witness material if such objects are packed in it.

In the embodiment of the system 100 shown, the containers 26A-26D may themselves serve as shipping or storage containers. In another embodiment of the system 100, containers 26A-26D may serve as internal containers, and may be packed within outer containers 26E, 26F, 26G, and 26H. As with internal containers 26A-26D, outer container 26E may be fitted with witness tape 22 on corners and edges of an external surface 46, and outer container 26F may be fitted with witness tape 22 on corners and edges of an internal surface 48. Outer container 26G may receive a coating 32 on an external surface 50, and/or or a coating 32 on an internal surface 52. Again, the coatings 32 and 34 on surfaces 50 and 52 may be concentrated on edges and corners because such locations are the most likely to receive impacts during shipping and/or storage. Outer container 26H may be enclosed in a shrink wrap 44 similar to that of container 26D. Application of witness material 10 may be at the time the outer containers 26E-26H are packed, or prior to packing and kept on hand.

The outer containers 26E-26H, or individual ones of them, or in the alternative, containers 26, 26A-26D without containers 26E-26H, containing the objects 24, 24A-24E packed within, may be loaded onto and transported on a vehicle 54, such as a land vehicle that may include a truck (e.g., a semitrailer), a train (e.g., a railcar), a delivery truck, or the like. Alternatively, or in addition, containers 26E-26H may be transported in a vehicle in the form of an aircraft 56, such as a cargo plane, jet aircraft, propeller-driven air craft, dirigible, and the like. The vehicles 54, 56 also may take the form of marine vehicles, such as cargo ships, barges, container ships (e.g., the containers 26E-26H travel in a sealed intermodal container), submarines, and the like. In an embodiment, one or more of the containers 26E-26H may take the form of an intermodal container of a type transported on a container ship. In addition, the vehicles 54, 56 may transport the object 24, 24A-24E to be stored in a storage facility, such as a warehouse 57, which may involve offloading the container 26E-26H from the vehicle, storing it or them in the storage facility, then reloading it or them back onto the vehicle, or onto another vehicle or form of vehicle.

Figure 4:
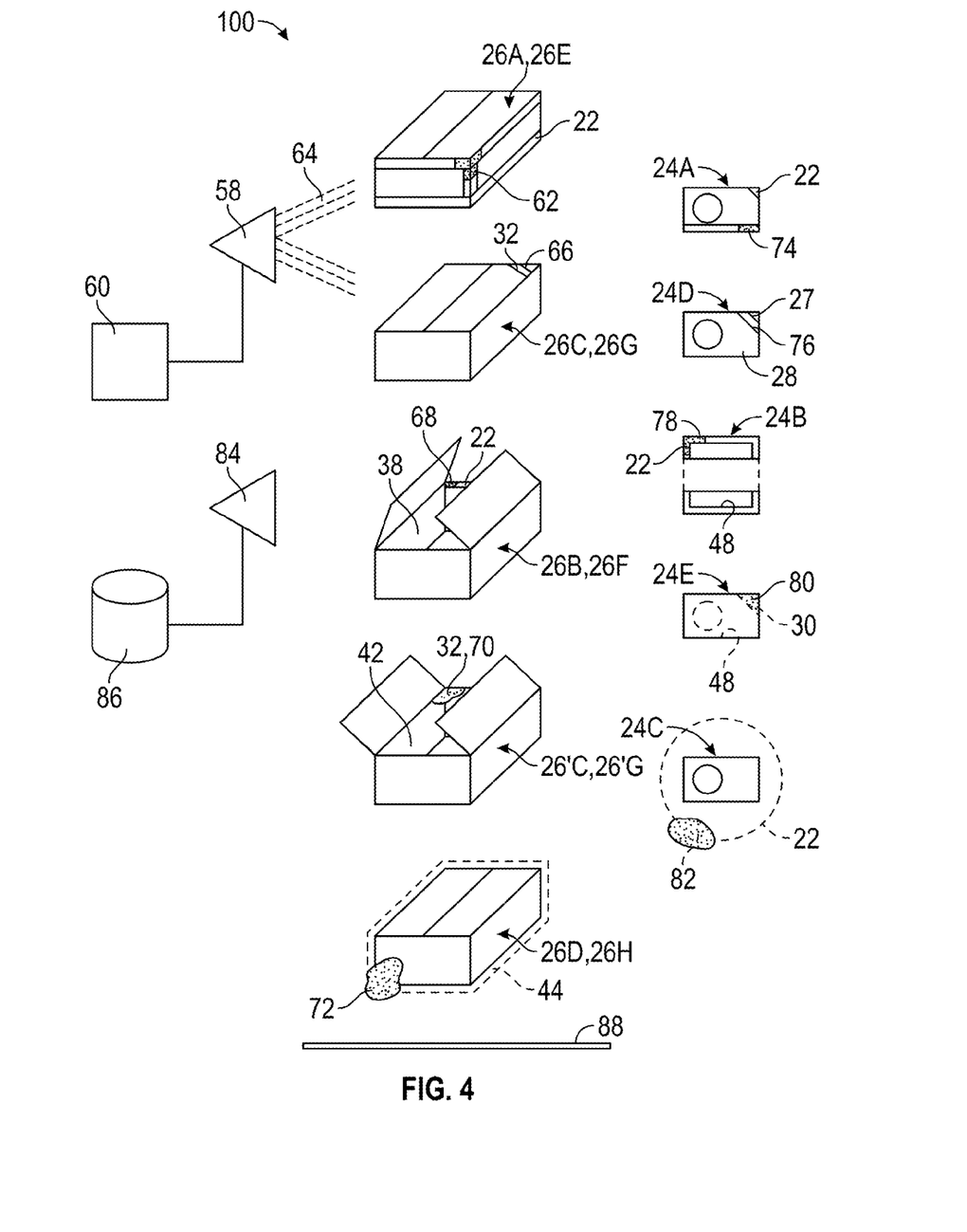
FIG. 4 is a schematic showing the process of directing actinic radiation on the witness material after the preparation and transportation depicted in FIG. 3.

As shown in FIG. 4, after the containers 26A-26H have been transported by vehicles 54 and/or 56, and optionally stored in warehouse 57, they may be offloaded at the location of the recipient of the object 24 and tested. The system 100 may include testing in the form of nondestructive testing for stress that the object 24 may have been subjected to during its transportation and possible storage from the sender to the recipient (i.e., while in the custody of the shipper or transporter). The testing may include irradiating the coating 16, 27, and/or 32 of the material with actinic radiation 64 from, for example, an ultraviolet light 58 energized by a power source 60. The irradiation or illumination 64 with such an ultraviolet light 58 may cause fluorescing of the coating 16, 27, 32 that shows discoloration in the form of one or both of a shift in color and/or a change in intensity of color in the coatings of the witness material 10 resulting from an externally applied stress.

For example, when illuminated by actinic radiation 64 from the ultraviolet light projector 58, the tape 22 on the container 26A may fluoresce and exhibit a discoloration in the form of a shift in color and/or a change in intensity of the color in the coating 16, indicated at 62, in an area on the container 26A that may have been subjected to an externally applied stress, such as an impact or shock above a predetermined level. Alternatively, or in addition, the discoloration 62 may result from heating the container 26A, or an area of localized heating of the container 26A, above a predetermined temperature beyond a predetermined time interval. The impact and/or elevated temperature and time collectively or individually may be considered a predetermined event that may result in damage to the object 24 that is shipped within the container 26A.

If the container takes the form of container 26C, exposure to actinic radiation 64 from projector 58 may reveal a discoloration in the fluorescing at 66, in an area that has received a coating 32 of witness material, the discoloration caused by a predetermined stress in the form of an impact and/or heating, the latter of which may be localized and for a predetermined time interval. Such discoloration 66 may indicate an impact in that area, and/or an area of localized heating above a predetermined temperature for a predetermined time, during transportation and/or storage during transportation.

As shown with reference to container 26B, the tape 22 on an interior surface 38 of the container that has been subjected to an impact or an elevated temperature for a predetermined period of time may exhibit discoloration when it fluoresces in response to radiation 64 from projector 58, as indicated at 68. As shown with reference to container 26'C, when that container is opened and the object 24 removed from it, the container may be irradiated by source 58 to receive actinic radiation 64 in the form of ultraviolet light which, when directed at the interior 42 of the container, may cause the coating 34 to discolor at 70 when it fluoresces in a shifted color or a change in intensity due to the stress event.

With respect to the container 26D, prior to removing the shrink wrap 44, the shrink wrap may be illuminated with actinic radiation 64 from the ultraviolet lamp 58 and an area 72 show discoloration when it fluoresces that may indicate an impact or an area of localized heating beyond a predetermined temperature and time interval. All of the foregoing indicators 62, 66, 68, 70, 72 may be relied upon by the recipient of the object 24 as evidence that the container 26A-26D, and the object 24 contained therein where subjected to an undesirable impact, and/or heating above a predetermined temperature for a predetermined time during shipment and/or storage during shipment.

Also as shown in FIG. 4, the same methodology may be applied to the container 26E with witness tape 22 on an outside surface 46 thereof, container 26F with witness tape 22 on an insider surface thereof, container 26G with a spray coating 32 of witness material 10 on a outside surface 50 thereof, container 26'G with a coating 32 of witness material 10 on an inside surface thereof, and container 26H with a coating 72 of witness material 10 on a shrink wrap 44. Similarly, the object 24 itself, if treated to receive the coating 16, may be tested to determine whether it has been subjected to undesirable impact and/or elevated temperature. In specific embodiments, object 24A that carries tape 22 (see FIG. 1) may display a discoloration when it fluoresces when illuminated by actinic radiation 64 in a shift in color or intensity 74, object 24D may display a discoloration 76 in coating 27 on an exterior surface 28 of the object 24D, object 24B may, when irradiated, display a discoloration 78 in a tape 22 on an interior surface 48 of the object 24B, object 24E may display a discoloration 80 in coating 30 when irradiated on the interior surface 48, and the shrink wrap 22 may when irradiated display a discoloration 82 adjacent object 24C.

In an embodiment, the system 100 may include an imaging device 84 that may take the form of a video camera or camera that can record the changes 62, 66, 68, 70, 72, 74, 76, 78, 80, 82 and store digital images in storage 86 as evidence of damage sustained to the object 24 during transportation and/or storage. In another embodiment, the containers 26A-26H, and/or the objects 24A-24E, may be placed on a conveyor 88 and moved beneath the ultraviolet light projector 58 and imaging device 84 so that they may be irradiated, and damage detected by the imaging device and stored in storage 86. Thus, the operation of illuminating the containers 26A-26H and/or objects 24A-24E may be automated by placing the containers and/or objects on the conveyor 88 and allowing them to pass serially by the illuminating device 58 and imaging device 84. The system may be automated and the imaging device 84 and storage 86 may provide a method of quantifying the detected changes in fluorescent intensity or color using image analysis software, or a fluorometer.

The disclosed witness material and method for monitoring the environmental history of the object 24 thus provides a non-destructive methodology for determining whether an object that has been shipped or stored has been subjected either to an undesirable impact above a predetermined stress level, and/or subjected to heating stress above a predetermined temperature for a predetermined time interval, which may damage the object, or the contents of the object. The object 24 may comprise sensitive electronic components, biological material, live animals, paint, chemicals, and other objects sensitive to temperature and impact. The coating 16 may be sprayed and applied to cover the tape 12 entirely, or may be sprayed in a pattern on the tape, or in a pattern on the container 26 or object 24.

While the forms of apparatus and methods described herein constitute preferred embodiments of the witness material and method for monitoring the environmental history of an object, it is to be understood that changes made be made therein without departing from the scope of the invention.

What is claimed is:

1. A witness material for monitoring an environmental history of an object, packed within a container, in particular transportation of the object by a vehicle, the witness material comprising:
   a material containing a dye of a type that fluoresces in response to actinic radiation in one or both of a shift in color and a change in intensity when subjected to a predetermined stress above a predetermined level, the predetermined stress including impact upon the object during the transportation; and
   the material forming a spray coating on only on a corner or edge of the container.

2. The witness material of claim 1, wherein the predetermined stress includes temperature.

3. The witness material of claim 1, wherein the predetermined stress includes temperature, and the material contains a dye of a type that fluoresces in response to actinic radiation in one or both of a shift in color and a change in intensity when subjected to the predetermined stress above the predetermined level for a predetermined time interval.

4. The witness material of claim 1, wherein the dye is of a type that fluoresces in response to actinic radiation other than visible light.

5. The witness material of claim 1, wherein the actinic radiation is ultraviolet light.

6. The witness material of claim 1, wherein the material includes a resin containing the dye.

7. The witness material of claim 1, wherein the dye is selected from a mechanochromatic dye and a thermochromatic dye.

8. The witness material of claim 1, further comprising a sprayer for spraying the coating on the interior surface of the container containing the object prior to the transportation.

9. The witness material of claim 8, wherein the spray coating is applied to a selected portion or portions of the interior surface of the container containing the object.

10. The witness material of claim 8, wherein the spray coating is applied only to one or both of edges and corners of the interior surface of the container containing the object.

11. The witness material of claim 1, wherein the container containing the object is a shrink wrap enclosing the object, preferably a shrink-wrappable sheet.

12. The system of claim 1, wherein the surface is an interior surface of the container.

13. A system using witness material for monitoring an environmental history of an object, in particular transportation of the object by a vehicle, the system comprising:
    a material containing a dye of a type that fluoresces in response to actinic radiation in one or both of a shift in color and a change in intensity when subjected to a predetermined stress above a predetermined level occurring during the transportation of the object by the vehicle, the stress including an impact;
    the material forming a spray coating on a surface of the object; and
    a source of the actinic radiation, the source configured to direct the actinic radiation on the coating after the transportation of the object by the vehicle, in response to the predetermined event.

14. The system of claim 13, wherein the source of actinic radiation is an ultraviolet light.

15. The system of claim 13, wherein the predetermined event is selected from an impact above a predetermined level upon the object and a heating above a predetermined level of the object.

16. The system of claim 13, wherein the surface is an interior surface of the object.

17. A method for monitoring an environmental history of an object, in particular transportation of the object by a vehicle, the method comprising:
    packing the object within a container;
    providing a material containing a dye of a type that fluoresces in response to actinic radiation in one or both of a shift in color and a change in intensity when subjected to a predetermined stress above a predetermined level;
    spray coating the material on a surface of the container; and
    examining the spray coating on the surface of the container after the transportation by the vehicle of the object within the container by applying the actinic radiation to determine whether the material fluoresces in response thereto to detect that the object has been subjected to the predetermined stress above the predetermined level during the transportation of the object by the vehicle.

18. The method of claim 17, further comprising irradiating the spray coating of the material with the actinic radiation to determine whether one or both of the shift in color and the change in intensity has occurred.

19. The method of claim 18, further comprising one or both of documenting and measuring the presence of the one or both of a shift in color and a change in intensity in the material after a predetermined event.

20. A system using witness material for monitoring an environmental history of an object, in particular transportation of the object by a vehicle, the system comprising:
   a material containing a dye of a type that fluoresces in response to actinic radiation in one or both of a shift in color and a change in intensity when subjected to a predetermined stress above a predetermined level, the stress including an impact;
   the material forming a coating on one or more of an inner container for the object enclosed within an outer container for the object, on an adhesive-backed tape that is applied to the inner container for the object, and an interior surface of the object;
   a source of the actinic radiation, the source configured to direct the actinic radiation on the coating after the transportation of the object by the vehicle in response to a predetermined event occurring during the transportation of the object by the vehicle; and
   a device for recording the one or both of the shift in color and the change in intensity when the material fluoresces in response to the actinic radiation after the transportation of the object by the vehicle in response to the predetermined event, the device for recording including one or both of a camera and a video camera.

21. The system of claim 20, wherein the device for recording includes a component for measuring the one or both of shift in color and the change in intensity, the component selected from image analysis software and a fluorometer.

* * * * *